United States Patent
Afzali-Ardakani et al.

(10) Patent No.: US 6,825,358 B2
(45) Date of Patent: Nov. 30, 2004

(54) SYNTHESIS OF SOLUBLE DERIVATIVES OF SEXITHIOPHENE AND THEIR USE AS THE SEMICONDUCTING CHANNELS IN THIN-FILM FIELD-EFFECT TRANSISTORS

(75) Inventors: Ali Afzali-Ardakani, Yorktown Heights, NY (US); Tricia Lynn Breen, Tarrytown, NY (US); Cherie Renee Kagan, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 10/057,024

(22) Filed: Jan. 25, 2002

(65) Prior Publication Data

US 2002/0072618 A1 Jun. 13, 2002

Related U.S. Application Data

(62) Division of application No. 09/614,232, filed on Jul. 12, 2000, now Pat. No. 6,414,164.

(51) Int. Cl.$^7$ ............................................. C07D 409/00
(52) U.S. Cl. ......................................................... 549/59
(58) Field of Search .............................. 549/59; 257/40; 438/99

(56) References Cited

U.S. PATENT DOCUMENTS 6,403,809 B1 * 6/2002 Holmes et al. ................ 549/41

\* cited by examiner

Primary Examiner—Deborah C. Lambkin
(74) Attorney, Agent, or Firm—Daniel P. Morris

(57) ABSTRACT

In accordance with the first object of this invention soluble derivatives of sexithiophene in which terminal carbons are substituted with various polar groups such as phosphonic esters, phosphonic acids, phosphonates, carboxylic acids, carboxylates, amines, amides, carbamates, and alcohols, each separated from the terminal thiophene rings by one or more methylene groups, are synthesized. An TFT device in accordance with the second objective of this invention employs films of the above sexithiophene derivatives as the semiconducting component. These organic semiconductors are dissolved in common organic solvents and applied to the surface of a substrate using inexpensive, low-temperature solution-based processing such as spin-coating, dip-coating, drop-casting, or microcontact printing.

10 Claims, 3 Drawing Sheets

SYNTHESIS OF SOLUBLE DERIVATIVES OF SEXITHIOPHENE AND THEIR USE AS THE SEMICONDUCTING CHANNELS IN THIN-FILM FIELD-EFFECT TRANSISTORS

This application is a division of Ser. No. 09/614,232 Jul. 12, 2000, U.S. Pat. No. 6,414,164.

FIELD OF INVENTION

This invention relates to the synthesis of various abed substituted sexithiophenes which have significant solubility in common organic solvents suitable for solvent casting and their use as the semiconducting channel in organic thin-film field-effect transistors.

BACKGROUND OF THE INVENTION

Thin film transistors, known as TFT's are widely used as switching elements in electronics, most notably for large area applications such as active matrix liquid crystal displays, smart cards etc. The Thin Film Transistor (TFT) is an example of a field effect transistor (FET). The best known example of an FET is the MOSFET (Metal-Oxide-Semiconductor-FET), today's conventional switching element for high speed applications.

Presently, TFT's in most devices are made using amorphous silicon as the semiconductor. Amorphous silicon provides a less expensive alternative to crystalline silicon—a necessary condition for reducing the cost of transistors in large area applications. Application of amorphous silicon is limited to low speed devices, since its mobility (0.1–0.5 $cm^2/V*sec$) is 15–20 thousand times smaller than that of crystalline silicon. Even though amorphous silicon is cheaper to deposit than highly crystalline silicon, deposition of amorphous silicon requires relatively costly processes, such as plasma enhanced chemical vapor deposition, and high temperatures (~360° C.) to achieve electrical characteristics sufficient for display applications.

In the past decade organic semiconductors have received much attention as potential semiconductor channels in TFTs, for example, U.S. Pat. No. 5,347,144 to Garnier et al., entitled "Thin-Layer Field-Effect Transistors with MIS Structure Whose Insulator and Semiconductors Are Made of Organic Materials". Organic materials (small molecules, short-chain oligomers and polymers) may provide a less expensive alternative to inorganic materials (e.g., amorphous silicon) for TFT applications as they are simpler to process, especially those that are soluble in organic solvents and therefore can be applied to large areas by far less expensive processes, such as spin-coating, dip-coating and microcontact printing. Furthermore organic materials may be deposited at low temperatures opening up a wider range of substrate materials including plastics for flexible electronic devices.

Several short-chain and oligomeric organic materials have been synthesized (e.g., α-sexithiophene) and have demonstrated mobilities close to amorphous silicon (0.1–0.6 $cm^2/V*sec$); however, these relatively high mobilities have only been achieved by high-temperature vacuum deposition, since most of these compounds are not soluble in organic solvents. Some soluble long-chain organic compounds (e.g., polyalkylthiophenes) have been synthesized which have mobilities of 0.001–0.01 $cm^2/V*sec$, but these materials usually have low on-off ratios, they must be applied under an atmosphere of inert gas and they must be extensively treated with base to reduce unintentional dopants introduced during polymerization to show semiconducting effects.

Accordingly, it is an object of this invention to synthesize soluble derivatives of the oligomer sexithiophene which are symmetrically substituted at the α- and ω- positions with various functional groups.

It is another object of this invention to use these derivatives of sexithiophene as low-cost, low-temperature alternatives to amorphous silicon as the semiconducting component in TFT devices.

SUMMARY OF THE INVENTION

A broad aspect of the present invention are soluble derivatives of sexithiophene in which terminal carbons are substituted with various polar groups such as phosphonic esters, phosphonic acids, phosphonates, carboxylic acids, carboxylates, mines, amides, carbamates, and alcohols, each separated from the terminal thiophene rings by one or more methylene groups, are synthesized. An TFT device in accordance with the second objective of this invention employs films of the above sexithiophene derivatives as the semiconducting component. These organic semiconductors are dissolved in common organic solvents and applied to the surface of a substrate using inexpensive, low-temperature solution-based processing such as spin-coating, dip-coating, drop-casting, or microcontact printing.

DETAILED DESCRIPTION OF THE INVENTION

Part A: Synthesis of sexithiophene derivatives.

This invention describes the synthesis of various derivatives of sexithiophene (7 R=H, n=0), which are soluble in common organic solvents at room temperature. Application of these compounds as the semiconducting components of an TFT device is also described in this invention.

Figure 1:
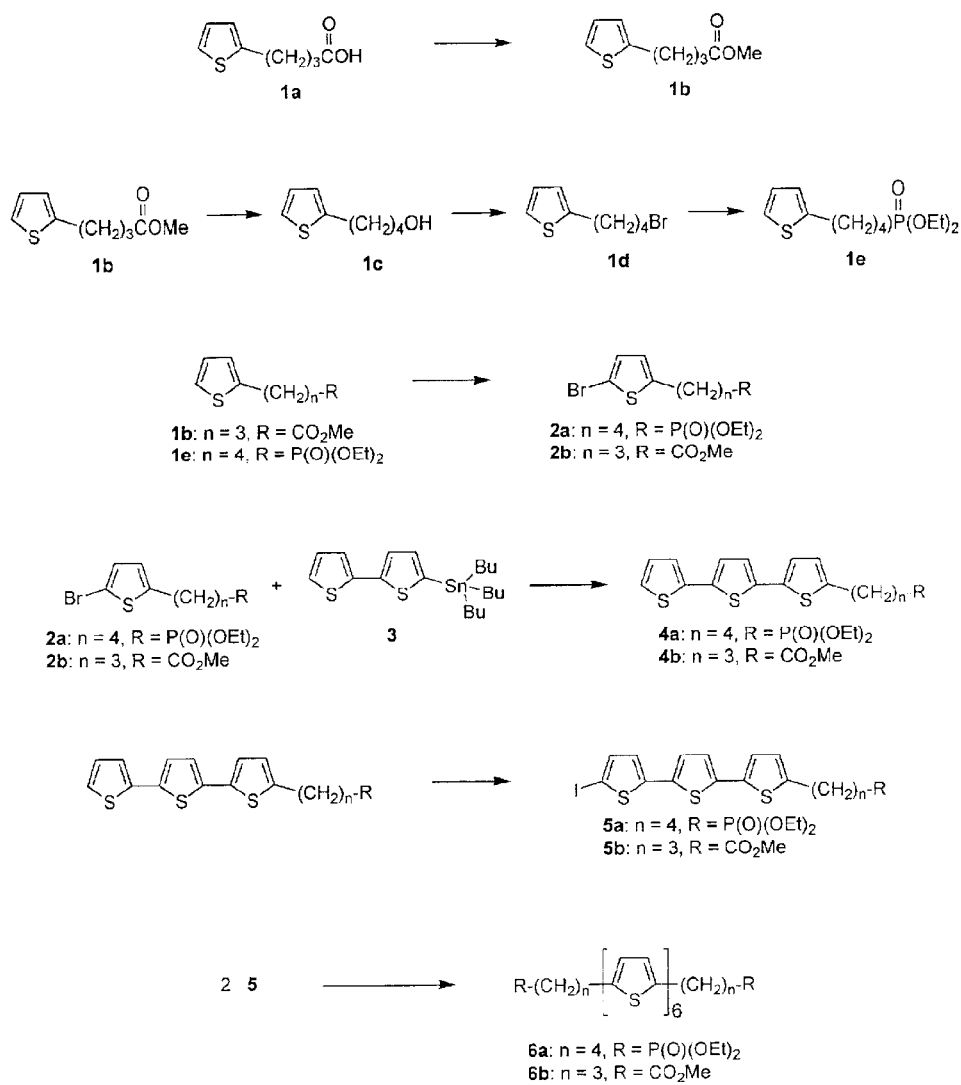
FIG. 1 depicts the synthetic scheme by which all substituted sexithiophenes of this invention are synthesized.

The synthetic scheme as shown in FIG. 1 employs two common steps for all derivatives. The first is conversion of substituted bromothiophenes 2 to substituted terthiophenes 4 via the palladium-catalyzed Stille coupling reaction as described by Frechet et al. (*J. Am. Chem. Soc.* 1998, 120, 10990) the teaching which is incorporated herein by reference. The second step is an improved Ullmann coupling of bromo- or iodoterthiophenes of structure 5 to the desired sexithiophene derivatives 6. The starting material for the synthesis of diphosphonic ester 6a and dicarboxylic ester 6c was commercially available 4-(2-thienyl)butyric acid 1a. Esterification of 1a with dimethoxypropane gave the methyl ester 1b quantitatively. Lithium aluminum hydride reduction of 1b, followed by bromination, gave the corresponding bromobutyithiophene 1d, which was converted to phosphonatic ester 1e by the Arbuzov reaction. NBS bromination of 1e gave phosphonic ester 2a. A Stille coupling of 2a with tributylstannylbithiophene 3 afforded terthiophenebutylphosphonate 4a.

The standard method for the preparation of sexithiophene has been monometallation (monolithiation) of terthiophene derivatives followed by oxidative coupling of the lithiated terthiophene by various oxidizing agents, most notably by copper chloride as described by Gamier et al. (*J. Am. Chem. Soc.* 1993, 115, 8716) the teaching which is incorporated herein by reference. Although this method has been satisfactory with moderate yields, it cannot be used for terthiophene derivatives having base (e.g., butyllithium) sensitive groups like carboxylic esters, amides etc. We have devised a new procedure for the coupling of terthiophene derivatives which is universal for all substituted terthiophenes. It involves the halogenation (bromination or, preferably, iodination) of terthiophene derivatives, which are then coupled via a palladium-catlayzed Ullmann-type coupling in accordance with the procedure described by Rawal et al. (*Organic Lett.* 2000, I (8), 1205) the teaching which is incorporated herein by reference, resulting in good yields of the corresponding sexithiophene derivatives. Accordingly, terthiophenebutylphosphonate 4a was selectively iodinated at the α-carbon of the terminal ring by reaction with iodine in the presence of mercuric acetate to give iodoterthiophenebutylphosphonate 5a. The palladium-catalyzed Ullmann coupling of 5a afforded sexithiophene 6a. Compound 6a is highly soluble in chlorinated organic solvents such as methylene chloride, chlorform, trichloroethylene etc., and can be applied on any substrate by spin-coating, dip-coating, drop-casting or any other methods which are used for application of thin films of organic materials from solution. The R functionality in structure 6 can be chosen from any polar functionality which might enhance the solubility and/or hydrogen bonding of sexithiophene derivatives. Following the procedure outlined above, sexithiophene derivatives containing carboxylic esters and acids were also synthesized. Carboxylic ester 1b was brominated with NBS to give 2b, which was coupled with tributyltinbithiophene 3 to give terthiophene 4b. Iodination of 4b yielded 5b, which was coupled using the palladium-catalyzed Ullmann reaction to afford sexithiophene 6b in high yield. Although the synthesis of two examples of sexithiophene (with phosphonate ester and carboxylic ester groups) is described, the same procedure can easily be used to prepare sexithiophene compounds substituted with other polar functionalities. For example, R in structure 6 can be chosen to be hydroxyl, amine, mercaptan, amides, carbamate, aldehyde, ketone, sulfonic acid, boronic acid or esters. At the same time, the methylene spacer groups which separate these functionalities from the thiophene rings may vary from 0 to 18 methylene groups, preferably from 1 to 10 methylene units.

EXAMPLE I

Detailed Synthetic Procedure for Synthesis of 6a

Methyl-4-(2-thienyl)butyrate 1b Concentrated hydrochloric acid (0.5 mL) was added to a solution of 4-(2-thienylbutyric acid) (10.0 g, 0.058 mol) in 100 mL of 2,2-dimethoxypropane and the resulting solution was stirred at room temperature for 48 hours. Excess dimethoxypropane was evaporated, and the oily residue was distilled under vacuum (105° C., 0.15 mm Hg) to yield methyl ester 1 b (10.2 g, 95%) as a colorless oil. IR: 1732 $cm^{-1}$ (ester carbonyl). $^1$H NMR (250 MHz, 25° C., $CDCl_3$):δ 7.11 (m, 1H, Ar—H), 6.91 (m, 1H, Ar—H), 6.78 (m, 1H, Ar—H), 3.66 (s, 3H, $OCH_3$), 2.87 (t, 2H, $CH_2CO_2Me$), 2.36 (t, 2H, Ar—$CH_2$), 2.00 (tt, 2H, $CH_2CH_2CH_2$).

2-(4-Hydroxybutyl)thiophene 1c. A 2.5 M solution of lithium aluminum hydride in THF (10 mL) was slowly added to a solution of methyl ester 1b (7.30 g, 0.04 mol,) in 100 mL of anhydrous THF. After completion of the addition, the solution was refluxed for four hours, then cooled to room temperature. Hydrochloric acid (10%, 25 mL) was then slowly added, and the resulting mixture was heated for another 30 minutes. After cooling to room temperature, diethyl ether (100 mL) was added, the organic layer was separated and washed with brine, dried with anhydrous magnesium sulfate. Evaporation of the solvent gave the alcohol 1c (5.4 g, 90%) as a colorless oil. $^1$H NMR (250 MHz, 25° C., $CDCl_3$): δ 7.12 (m, 1H, Ar—H), 6.92 (m, 1H, Ar—H), 6.79 (m, 1H, Ar—H), 3.62 (t, 2H, $CH_2OH$), 2.86 (t, 2H, Ar—$CH_2$), 2.30 (s, 1H, OH), 2.00 (m, 4H, $CH_2CH_2CH_2CH_2$).

2-(4-Bromobutyl)thiophene 1d. Chlorotrimethylsilane (2.60 g, 0.025 mol) was added to a solution of lithium bromide (1.75 g, 0.02 mol) in 100 mL of anhydrous acetonitrile and the mixture was stirred under nitrogen for 30 minutes. To this solution was added, via syringe, a solution of alcohol 1c (1.56 g, 0.01 mol) in 10 mL of acetonitrile and the resulting solution refluxed overnight. The solution was cooled to room temperature, the solvent was evaporated under reduced pressure and the residue was taken up in diethyl ether. The solid was removed by filtration, and the filtrate was evaporated to give an oily brown residue which was purified by flash chromatography through a column of silica gel using hexane as the eluent, to give bromobutylthiophene 1d (1.9 g, 88%) as a colorless oil. $^1$H NMR (250 MHz, 25° C., $CDCl_3$): δ 7.10 (m, 1H, Ar—H), 6.91 (m 1H, Ar—H), 6.78 (m, 1H, Ar—H), 3.41 (t, 2H, $CH_2Br$), 2.85 (t, 2H, Ar—$CH_2$), 1.85 (m, 4H, $CH_2CH_2CH_2CH_2$).

Diethyl-4-(2-thienyl)butylphosphonate 1e. A solution of 1d (4.58 g, 0.02 mol) in 20 mL of triethylphosphite was heated at 160° C. for 20 hours, with nitrogen bubbling directly into the solution. The solution was cooled to room temperature and 50 mL of water was added; the resulting mixture was stirred for 4 hours. The product was extracted with methylene chloride, the organic layer was separated and washed with brine, then dried over anhydrous magnesium sulfate. Evaporation of the solvent yielded an oily residue, which was distilled under vacuum (0.12 mm Hg, 135° C.) to give 1e as a colorless oil (6.0 g, 82%). $^1$H NMR (250 MHz, 25° C., $CDCl_3$): δ 7.06 (m, 1H, Ar—H), 6.85 (m, 1H, Ar—H), 6.72 (m, 1H, Ar—H), 4.03 (m, 4H, $POCH_2CH_3$), 2.79 (t, 2H, Ar—$CH_2$), 1.72 (m, 6H, $CH_2CH_2CH_2P$), 1.26 (t, 6H, $POCH_2CH_3$).

Diethyl-4-(2-bromothienyl)butylphosphonate 2a. N-bromosuccinimide (1.78 g, 0.01 mol) was added portionwise to a solution of 1e (2.78, 0.01 mol) in dimethylformamide (20 mL) and the solution was stirred at room temperature overnight. Diethyl ether (50 mL) was added to the reaction mixture, which was then washed twice (50 mL each) with water, once with brine, and dried over anhydrous magnesium sulfate. Evaporation of the solvent gave 2a as light yellow oil (3.2 g, 87%)$^1$H NMR (250 MHz, 25° C., $CDCl_3$): δ 6.80 (d, 1H, Ar—H), 6.49 (d, 1H, Ar—H), 4.03 (m, 4H, $POCH_2CH_3$), 2.72 (t, 2H, Ar—$CH_2$), 1.67 (m, 6H, $CH_2CH_2CH_2P$), 1.27 (t, 6H, $POCH_2CH_3$).

Diethyl-4-[5-(2,2':5'2")terthienyl]butylphosphonate 4a. 5-tributylstannyl-(2,2')bithiophene (4.54 g, 0.01 mol) was added to a solution of 2a (3.55 g, 0.01 m 1) in anhydrous DMF (30 mL) under a nitrogen atmosphere. To this solution was added 500 mg of bis(triphenylphosphine)palladium(II) chloride and the mixture was heated to 60° C. for 3 hours and then stirred at room temperature for 20 hours. Diethyl ether (100 mL) was added and the mixture was washed several times with water and then with brine, and dried over anhydrous magnesium sulfate. Evaporation of the solvent gave a yellow-orange solid residue, which was chromatographed on column of silica gel. Elution with ethyl acetate gave, after evaporation of the solvent, an orange solid (3.0 g, 83%). Crystallization from hexane afforded analytically pure 4a. m.p.: 92° C. $^1$H NMR (250 MHz, 25° C., CDCl$_3$): δ 7.16-6.94 (m, 6H, Ar—H), 6.66 (m, 1H, Ar—H), 4.08 (m, 4H, POCH$_2$CH$_3$), 2.79 (t, 2H Ar—CH$_2$), 1.75 (m, 6H, CH$_2$CH$_2$CH$_2$P), 1.29 (t, 6H, POCH$_2$CH$_3$).

Diethyl-4-[5"-iodo-5-(2,2":5'2"-terthienyl)butylphosphonate 5a. Mercuric acetate (0.954 g, 3 mmol) was added to a solution of 4a (2.28 g, 5 mmol) in anhydrous DMF (20 mL) and the mixture was stirred at room temperature for one hour under nitrogen. Iodine (1.27 g, 5 mmol) was then added to the solution portionwise over a period of 30 minutes and the mixture stirred at room temperature for 20 hours. Diethyl ether (50 mL) was added and the solution was washed several times with water and then with brine, and dried over anhydrous magnesium sulfate. Evaporation of the solvent gave an orange solid residue which was crystallized from a mixture of toluene and hexane (50:50 v:v) to give 5a (2.5 g, 91%) as an orange microcrystalline compound, m.p.: 115° C. $^1$H NMR (250 MHz, 25° C., CDCl$_3$): δ 7.12 (m, 1H, Ar—H), 6.94 (m, 3H, Ar—H), 6.78 (m, 1H, Ar—H), 6.66 (m, 1H, Ar—H), 4.05 (m, 4H, POCH$_2$CH$_3$), 2.79 (t, 2H, Ar—CH$_2$), 1.70 (m, 6H, CH$_2$CH$_2$CH$_2$P), 1.29 (t, 6H, POCH$_2$CH$_3$).

Bis-Diethyl-4-[(5,2'''''-(2,2':5'2":5''',2''':5'''',2''''':5''''',2'''''-sexithiophenediyl)-butylphosphon ate 6a. A solution of palladium acetate (20 mg, 0.09 mmol) and tri-p-tolylphosphine (30 mg, 0.1 mmol) in anhydrous DMF (10 mL) was added to a mixture of 5-iodo-2,2':5',2"-terthienylbutylphosphonate 5a (950 mg, 1.67 mmol), hydroquinone (160 mg, 1.4 mmol) and cesium carbonate (700 mg, 2.1 mmol), and the mixture was deaerated by three freeze-thaw cycles and backfilled with nitrogen. The mixture was then heated at 70° C. for 4 hours, cooled to room temperature and then stirred further for 20 hours. The dark orange solid was separated by filtration, washed several times with diethyl ether, and dried in vacuo. Crystallization from 1,2-dichlorobenzene afforded 6a as a bright red-orange microcrystalline product (900 mg, 62%). m.p. (measured by DSC): 245° C.

EXAMPLE II

Detailed Synthetic Procedure for Synthesis of 6b

Methyl-4-(5-bromo-2-thienyl butyrate 2b. The NBS bromination of 1b according to the procedure outlined for the preparation of 2a gave > 90% yield of 2b as a colorless oil. b.p.: 138° C. at 0.15 mmHg. $^1$H NMR (250 MHz, 25° C., CDCl$_3$): δ 6.82 (d, 1H, Ar—H), 6.52 (d, 1H, Ar—H), 3.64 (s, 3H, OCH$_3$), 2.79 (t, 2H, CH$_2$CO$_2$Me), 2.33 (t, 2H, Ar—CH$_2$), 1.93 (tt, 2H, CH$_2$CH$_2$CH$_2$).

Methyl-4-(5-2,2':5',2"-terthienyl)butyrate 4b. The Stille coupling reaction of 2b with 5-tributylstannyl-2,2'-bithiophene 3 according to the procedure outlined for the preparation of 4a gave the terthiophene derivative 4b in 80% yield as a fluorescent yellow solid, m.p.: 81° C. $^1$H NMR (250 MHz, 25° C., CDCl$_3$): δ 7.20-7.13 (m, 2H, Ar—H), 7.04-6.95 (m, 4H, Ar—H), 6.68 (m, 1H, Ar—H), 3.66 (s, 3H, OCH$_3$), 2.84 (t, 2H, CH$_2$CO$_2$Me), 2.38 (t, 2H, Ar—CH$_2$), 1.99 (tt, 2H, CH$_2$CH$_2$CH$_2$).

Methyl-4-[5-bromo-5"-(2,2':5',2"-terthienyl)]butyrate 5b. NBS bromination of 4b following the procedure outlined for 4a gave 5b in > 80% yield as a yellow-green solid. m.p.: 134° C. $^1$H NMR (250 MHz, 25° C., CDCl$_3$): δ 7.14 (m, 1H, Ar—H), 6.98 (m, 3H, Ar—H), 6.81 (m, 1H, Ar—H), 6.69 (m, 1H, Ar—H), 3.68 (s, 3H, OCH$_3$), 2.85 (t, 2H, CH$_2$CO$_2$Me), 2.39 (t, 2H, Ar—CH$_2$), 2.01 (tt, 2H, CH$_2$CH$_2$CH$_2$).

Sexithiophene 6b. A solution of tri-p-tolylphosphine (100 mg, 0.3 mmol) and palladium acetate (100 mg, 0.45 mmol) in 10 mL of anhydrous dimethylformamide was added to a mixture of 5b (600 mg, 1.25 mmol), hydroquinone (200 mg, 1.8 mmol) and cesium carbonate (400 mg, 1.25 mmol). The mixture was deaerated by three cycles of freeze-thaw, backfilled with nitrogen, and heated at 80° C. for 20 hours. The resulting black mixture was cooled to room temperature, the precipitate was filtered and washed thoroughly with ethanol and diethyl ether, and dried in vacuo. Crystallization from 1,2-dichlorobenzene afforded 6b as a red-orange crystalline compound. m.p.(DSC):

EXAMPLE III

Device Fabrication

Figure 2:
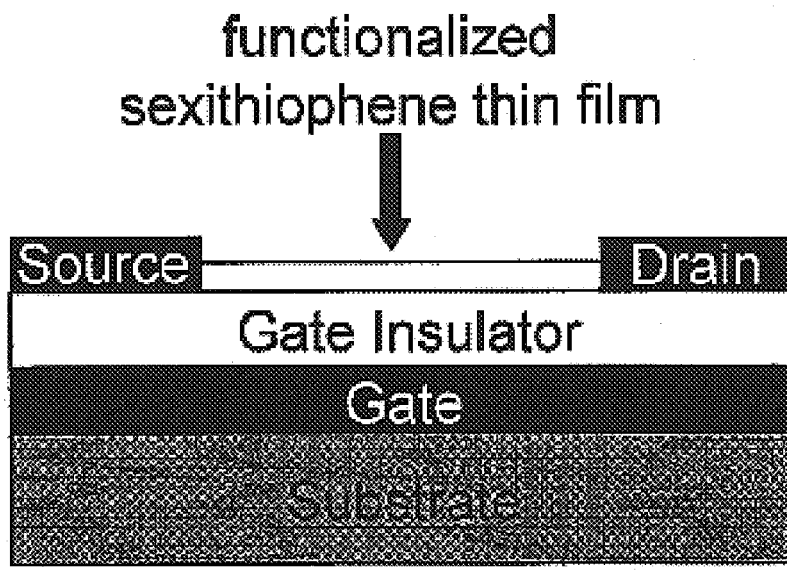
FIG. 2 is a cross-sectional view of the TFT structure incorporating a sexithiophene derivative of this invention as the semiconducting channel.
Figure 3:
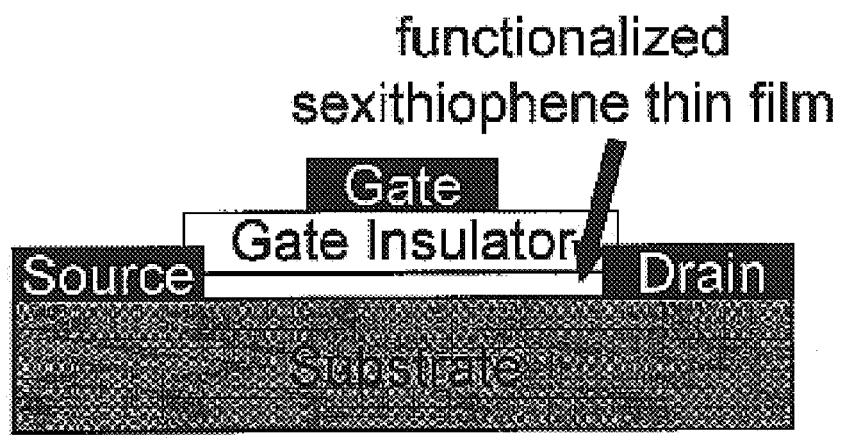
FIG. 3 illustrates elements of an alternative TFT structure.

The use of sexithiophene 6a as the semiconducting channel in a Thin Film Transistor (TFT) is exemplified as follows:

A thin film transistor was fabricated by spin coating (or drop casting) a solution of sexithiophene 6a in chloroform (2 mg/mL) on a highly doped silicon wafer, serving both as the gate electrode and substrate with a 500 nm thermally grown silicon dioxide as gate insulator and gold source and drain electrodes as shown in FIG. 2. While FIG. 2 illustrates a typical TFT structure arrangement, alternative structures are contemplated as within the ambit of the invention. See FIG. 3 where the respective elements of an alternative TFT structure are illustrated. Alternative substrates include plastics such as polyimide and polycarbonate, which may be used to build flexible devices.

Figure 4:
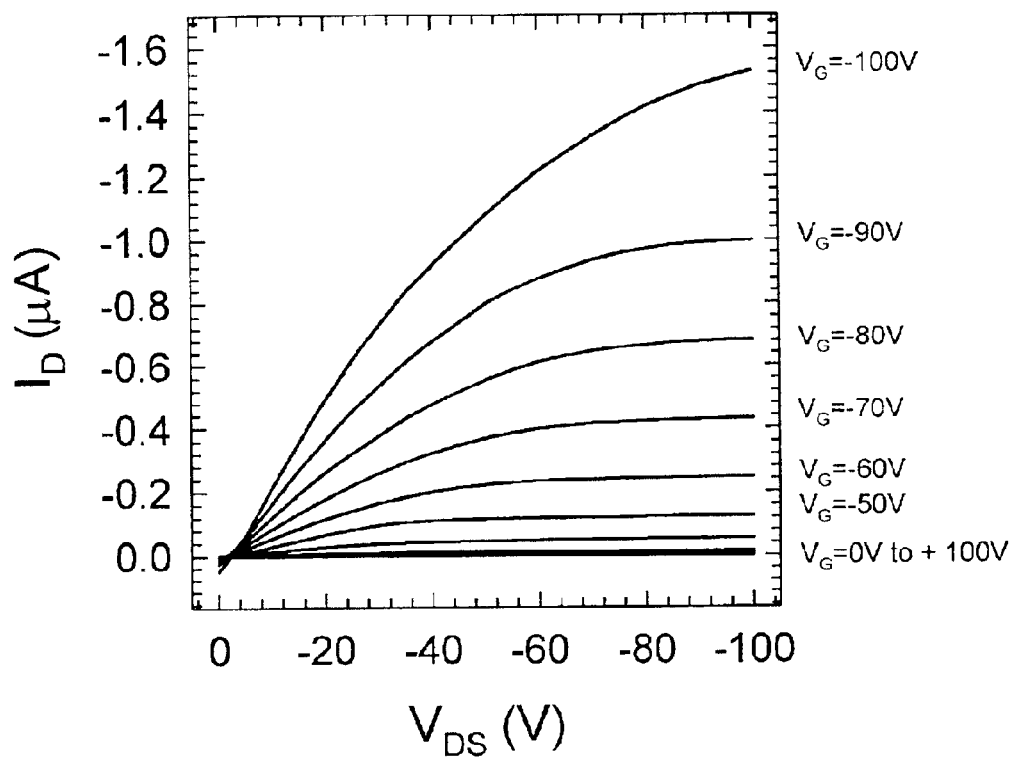
FIG. 4 is a plot of $I_D$ versus $V_{DS}$ for a TFT with sexithiophenedibutylphosphonate as the active semiconducting material.
Figure 5:
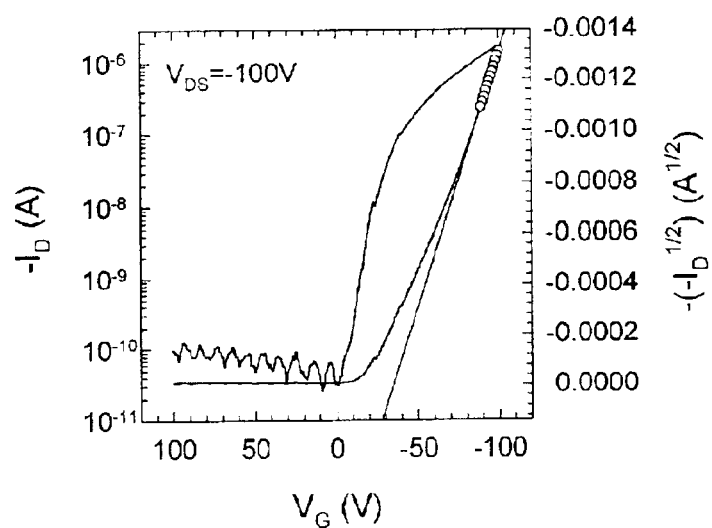
FIG. 5 is a plot of $I_D$ versus $V_G$ for a TFT with sexithiophenedibutylphosphonate as the active semiconducting material.

Preliminary data demonstrating the desired field-modulated conductance and current saturation for a TFT prepared with the soluble sexithiophene 6a are shown in FIGS. 4 and 5. The sexithiophene compound forms a p-channel transistor as shown in a plot of drain current, $I_D$, versus source-drain voltage, $V_{DS}$, as a function of gate voltage $V_G$ (FIG. 4). Device operation is modeled by standard field-effect transistor equations. Plots of $I_D$ and $I_D^{1/2}$ versus gate voltage, $V_G$ (FIG. 5), at $V_{DS}$=100 V are used to calculate the current modulation ($I_{on}/I_{off}$) and field-effect mobility in the saturation regime. For this device, with a channel width of 1.5 mm and a channel length of 28 micrometers, the current modulation is greater than $10^4$ and the field-effect mobility is $2.2*10^{-3}$ cm$^2$V-sec.

What is claimed is:

1. A composition of matter comprising a sexithiophene: where the a- and w-carbons of the terminal thiophene rings are substituted with alkyl groups having a polar functionality R at their terminal carbons;

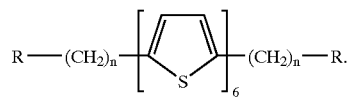

2. A composition of matter of claim 1, where the alkyl groups on both ends have from one to 10 carbons.

3. A composition of matter of claim 2, where alkyl groups on the terminal rings are substituted at their terminal carbon atoms by a polar functionality.

4. A composition of matter of claim 3, where the polar functionality is a dialkyl phosphonate group.

5. A composition of matter of claim 3, where the polar functionality is a phosphonic acid group.

6. A composition of matter of claim 3, where the polar functionality is a carboxylic acid group.

7. A composition of matter of claim 3, where the polar functionality is a carboxylic ester group.

8. A composition of matter of claim 3, where the polar functionality is an amino group.

9. A composition of matter of claim 3, where the polar functionality is an amide group.

10. A composition of matter of claim 3, where the polar functionality is a hydroxyl group.

* * * * *